(12) United States Patent
Meier et al.

(10) Patent No.: US 8,394,996 B2
(45) Date of Patent: Mar. 12, 2013

(54) METHOD FOR PRODUCING ALDEHYDE FUNCTIONAL COMPOUNDS

(75) Inventors: Michael A. R. Meier, Jockgrim (DE); Anastasiya Rybak, Denzlingen (DE); Dominik Geisker, Emden (DE); Peter Hannen, Herten (DE); Martin Roos, Haltern am See (DE)

(73) Assignee: Evonik Degussa GmbH, Essen (DE)

( * ) Notice: Subject to any disclaimer, the term of this patent is extended or adjusted under 35 U.S.C. 154(b) by 70 days.

(21) Appl. No.: 13/142,505

(22) PCT Filed: Jan. 12, 2010

(86) PCT No.: PCT/EP2010/050261
§ 371 (c)(1),
(2), (4) Date: Jun. 28, 2011

(87) PCT Pub. No.: WO2010/084053
PCT Pub. Date: Jul. 29, 2010

(65) Prior Publication Data
US 2012/0022276 A1 Jan. 26, 2012

(30) Foreign Application Priority Data
Jan. 23, 2009 (DE) .......................... 10 2009 005 951

(51) Int. Cl.
*C07C 45/00* (2006.01)
*C07C 249/00* (2006.01)
*C07C 29/00* (2006.01)
*C07C 33/00* (2006.01)

(52) U.S. Cl. ........ 568/459; 568/460; 568/904; 568/905; 568/908; 564/279; 554/114

(58) Field of Classification Search .................. 568/459, 568/460, 904, 905, 908; 564/279; 554/114
See application file for complete search history.

(56) References Cited

U.S. PATENT DOCUMENTS

| 6,013,816 | A | 1/2000 | Gelling et al. |
| 6,111,149 | A | 8/2000 | Schwab et al. |
| 6,828,449 | B2 | 12/2004 | Herwig et al. |
| 6,861,540 | B2 | 3/2005 | Herwig et al. |
| 6,927,308 | B2 | 8/2005 | Leininger et al. |
| 7,084,300 | B2 | 8/2006 | Herwig et al. |
| 7,253,329 | B2 | 8/2007 | Herwig et al. |
| 7,495,129 | B2 | 2/2009 | Balduf et al. |
| 7,608,738 | B2 | 10/2009 | Herwig et al. |
| 2007/0004903 | A1 | 1/2007 | Hoff et al. |
| 2007/0265184 | A1 | 11/2007 | Herwig et al. |
| 2009/0306367 | A1 | 12/2009 | Roos et al. |
| 2010/0312012 | A1 | 12/2010 | Hannen et al. |
| 2011/0015434 | A1 | 1/2011 | Hannen et al. |

FOREIGN PATENT DOCUMENTS

| WO | 95 18783 | 7/1995 |
| WO | 98 03456 | 1/1998 |

OTHER PUBLICATIONS

Finnegan, D., et al., "Preparation of Aliphatic Ketones through a Ruthenium-Catalyzed Tandem Cross Metathesis/Allylic Alcohol Isomerization," Organic Letters, vol. 8, No. 12, pp. 2603-2606, (May 17, 2006) XP 002574162.
International Search Report issued Apr. 6, 2010 in PCT/EP10/050261 filed Jan. 12, 2010.
U.S. Appl. No. 13/124,600, filed Apr. 15, 2011, Meier, et al.

*Primary Examiner* — Sikarl Witherspoon
(74) *Attorney, Agent, or Firm* — Oblon, Spivak, McClelland, Maier & Neustadt, L.L.P.

(57) ABSTRACT

The invention relates to a method for producing aldehyde functional compounds by a cross-metathesis reaction of an olefinic compound having at least one hydroxy group and at least one C—C double bond with at least one at least monounsaturated fatty acid or at least one at least monounsaturated fatty acid derivative, in the presence of a metathesis catalyst at a maximum temperature of 180° C. and in the presence of at least one reagent that acts as a protective group-forming compound in relation to the aldehyde group of the aldehyde functional compounds.

20 Claims, No Drawings

METHOD FOR PRODUCING ALDEHYDE FUNCTIONAL COMPOUNDS

The present invention relates to a process for preparing an aldehyde-functional compound by cross-metathesis reaction.

Processes for preparing aldehyde-functional compounds and a mixture comprising hydroxy- and aldehyde-functional compounds are known and are produced when, for example, carboxylic acid derivatives are reduced or alcohols are oxidized.

From the article by Marc L. Snapper et al. "Preparation of Aliphatic Ketones through a Ruthenium-Catalyzed Tandem Cross-Metathesis/Allylic Alcohol Isomerization" in Organic Letters, pp. 2603-2606 (2006) the reaction is known of bicyclic compounds, with ring-opening cross-metathesis (ROCM), with Z-1,4-butenediol, with reaction taking place to produce both the hydroxyl-functional and the aldehyde-functional product. Disclosed, furthermore, is the reaction of α,β-unsaturated 4-hydroxy alcohols functionalized in positions 1 and 4 to give the corresponding ketones.

Disadvantages associated with this process are the fact that isomerization requires a temperature of 200° C. and that significant quantities of over-reduced, i.e. saturated, hydroxyl compounds are produced. There is no mention of the use of fatty acids or their derivatives.

Metathesis reactions are employed extensively as part of chemical syntheses, in the form, for example, of ring-closing metathesis (RCM), cross-metathesis (CM) or ring-opening metathesis polymerization (ROMP). Metathesis reactions find application, for example, for olefin synthesis, for depolymerization of unsaturated polymers and for synthesis of telechelic polymers.

The self-metathesis of allyl alcohol, allyl cyanide and derivatives thereof with simultaneous isomerization is known, furthermore, from the article by Wagener et al. (J. Mol. Catal. A, Chemical 2003, 194, 69-78). An isomerization accompanying the self-metathesis was suppressed by means of certain solvents. Cross-metatheses were not disclosed.

It is an object of the present invention to provide a process for preparing aldehyde-functional fatty acid derivatives without producing significant amounts of hydroxyl-functional compounds, saturated alcohols and/or aldol addition products (i.e. less than 10% by weight). According to a further object of the present invention, this should result in less than 5% by weight of the aforementioned by-product.

This object is achieved by means of a process for preparing an aldehyde-functional compound by means of a reaction sequence consisting of cross-metathesis reaction and isomerization of an olefinic compound containing at least one hydroxyl group and at least one C—C double bond with at least one at least monounsaturated fatty acid or an at least monounsaturated fatty acid derivative, in the presence of a metathesis catalyst at a temperature of not more than 180° C. and also in the presence of at least one reactant acting as a compound forming protective groups with respect to the aldehyde group of the aldehyde-functional compounds.

The term "at least monounsaturated fatty acid" refers here and below to an unsaturated carboxylic acid which has a hydrocarbon radical having 1 to 50 C atoms. Preferred fatty acids have 4 to 50, more particularly 6 to 30 and especially 8 to 24 C atoms, such as 12 to 18 C atoms, for example. They may be natural or synthetic in origin. With particular preference they are natural in origin and offer an ideal starting platform based on renewable raw materials. They may carry substituents such as, for example, halogen atoms, halogenated alkyl radicals, cyano, hydroxyalkyl, methoxy, nitrile, nitro and/or sulphonic acid groups, with the proviso that they are stable under the reaction conditions and do not enter into any side reactions such as elimination reactions, for example. The at least monounsaturated hydrocarbon radicals may preferably be linear, branched or cyclic. With preference there is no double bond in α,β-position to the carboxyl group.

Unsaturated fatty acids suitable for the process of the invention include 3-hexenoic acid (hydrosorbic acid), trans-2-heptenoic acid, 2-octenoic acid, 2-nonenoic acid, cis- and trans-4-decenoic acid, 9-decenoic acid (caproic acid), 10-undecenoic acid (undecylenic acid), cis-4-dodecenoic acid (linderic acid), tridecenoic acid, cis-9-tetradecenoic acid (myristoleic acid), pentadecenoic acid, cis-9-hexadecenoic acid (cis-9-palmitoleic acid), trans-9-hexadecenoic acid (trans-9-palmitoleic acid), delta-7-cis,10-cis-hexadecadienoic acid, 9-heptadecenoic acid, cis-6-octadecenoic acid (petroselinic acid), trans-6-octadecenoic acid (petroselaidic acid), cis-9-octadecenoic acid (oleic acid), trans-9-octadecenoic acid (elaidic acid), cis-11-octadecenoic acid, trans-11-octadecenoic acid (vaccenic acid), cis-5-eicoseic acid, cis-9-eicoseic acid (gadoleic acid), cis-11-eicoseic acid (gondoic acid), cis-11,cis-14-eicosadienoic acid, cis-5,cis-8,cis-11,cis-14-eicosa-tetraenoic acid (arachidonic acid), cis-11-docosenoic acid (cetoleic acid), cis-13-docoseic acid (erucic acid), trans-13-docosenoic acid (brassidic acid), cis-15-tetracosenoic acid (selacholeic acid or nervonic acid), cis-17-hexacosenoic acid (ximenic acid) and cis-21-triacontenoic acid (lumequic acid), and also 2,4-hexadienoic acid (sorbic acid), cis-9-cis-12-octadecadienoic acid (linoleic acid), cis-9-cis-12-cis-15-octadecatrienoic acid (alpha-linolenic acid), cis-6-cis-9-cis-11-octadecatrienoic acid (gamma-linolenic acid), eleostearic acid, 12-hydroxy-cis-9-octadecenoic acid (ricinoleic acid), 9Z,12S,13R-epoxy-9-octadecenoic acid (vernolic acid), cis-5-docosenoic acid, cis-5,13-docosadienoic acid and similar acids.

Also suitable as reactants are unsaturated fatty acids having 10 to 22 carbon atoms, which can be obtained in the form of their technical mixtures with other fatty acids based on renewable natural raw materials, such as, for example, from sunflower oil, rapeseed oil, soybean oil, jatropha oil, castor oil, tall oil or fish oil. As is usual in the chemistry of fats, these polyunsaturated fatty acids are generally used not in the form of their pure compounds but instead in the form of their technical mixtures, in producing the products of the invention. The aforementioned fatty acids are preferably employed not only as they are but also in the form of their esters, with C1-C36 alkanols (alcohols), more particularly with C1-C4 alkanols. Typical examples of alkanols of this kind for forming esters with the aforementioned fatty acids are methanol, ethanol, n- and isopropanol, n- and isobutanol, n- and isopentanol, n- and isohexanol, n- and isooctanol, n- and iso-decanol, n- and isododecanol, n- and isotetradecanol, n- and isohexadecanol, n- and isooctadecanol, and also higher fatty alcohols and/or branched fatty alcohols and/or fatty alcohol derivatives having up to 36 carbon atoms, examples being C36 Guerbet alcohols. Polyhydric alcohols, such as glycerol, glycol, pentaerythritol or bispentaerythritol are also suitable for these reactions. The fatty acids can also be used in the form of their amides, nitriles, fatty alcohols and other derivatives.

A special preference is given to the corresponding esters with methanol, from which, in accordance with the process disclosed here, important starting products are obtained for the production of high-performance polymers (polyamides, polyesters, etc.).

The term "at least monounsaturated fatty acid derivative" also encompasses the corresponding alcohol.

The term "hydroxyl-functional fatty acid derivative" refers here and below to a compound which corresponds to one of the aforementioned fatty acid derivatives and additionally contains at least one OH group. Furthermore, the hydroxyl-functional fatty acid derivatives may be substituted and may have at least one functional group (such as, for example, ester, amide, nitrile, aldehyde, ketone etc). They may also carry substituents such as, for example, halogen atoms, halogenated alkyl radicals, cyano, hydroxyalkyl, methoxy, nitrile, nitro and/or sulphonic acid groups, with the proviso that they are stable under the reaction conditions and do not enter into any side reactions such as elimination reactions, for example.

The term "aldehyde-functional fatty acid derivatives" refers here and below to a compound which corresponds to one of the aforementioned fatty acids and additionally contains at least one aldehyde and/or keto group.

The term "at least monounsaturated fatty acid derivative" refers here and below to a compound which is obtained from the reaction with a fatty acid and contains an unsaturated hydrocarbon radical.

One example of such a fatty acid derivative is an unsaturated fatty acid ester. The alcohol segment of the fatty acid ester may be any monohydroxy, dihydroxy or polyhydroxy alcohol which is capable of condensation with an unsaturated fatty acid to form an ester. In seed oils the alcohol segment is glycerol, a trihydroxy alcohol. If desired, the glycerides can be converted by transesterification into fatty acid esters of lower alcohols, which can be separated off more easily or which are suitable for subsequent chemical operations. The alcohol used in the transesterification typically contains at least one carbon atom. The alcohol typically contains less than about 15 carbon atoms, preferably less than about 12 carbon atoms, more preferably less than about 10 carbon atoms, and even more preferably less than approximately 8 carbon atoms. The carbon atoms in the alcohol segment may be arranged in a linear chain or in a branched structure and may be substituted by a multiplicity of substituents, such as, for example, those disclosed beforehand herein in connection with the olefin reactants, including the abovementioned alkyl, cycloalkyl, monocyclic aromatic, arylalkyl, alkylaryl, hydroxyl, halogen, nitro, carboxylic acid, ether, ester, acyl and amide substituents. The alcohol segment of the unsaturated fatty acid ester is preferably glycerol or a straight-chain or branched C1-C8 alkanol. It most preferred if the alcohol is a C1-C3 alkanol; suitable examples thereof include methanol, ethanol and propanol.

Other fatty acid derivatives suitable for the process of the invention are fatty alcohols obtained by reduction from the fatty acids or fatty acid derivatives; esterified fatty alcohols; fatty amides, fatty amines (primary, secondary, tertiary), fatty nitriles; and long-chain unsaturated compounds containing a functional group. Examples of functional groups are all suitable functional groups known per se to the skilled person, such as, for example, halogen atoms, halogenated alkyl radicals, cyano, hydroxyalkyl, methoxy, nitrile, nitro, amino, hydroxyl and/or sulphonic acid groups.

The term "olefinic compound containing at least one hydroxyl group and at least one C—C double bond" refers here and below to a compound of this type which has an unsaturated hydrocarbon radical having 3 to 10 carbon atoms.

Examples thereof are prop-2-en-1-ol (allyl alcohol), but-3-en-1-ol, pent-4-en-1-ol, hex-5-en-1-ol, hept-6-en-1-ol, oct-7-en-1-ol, non-8-en-1-ol and dec-9-en-1-ol. Examples of unsaturated diols are but-2-ene-1,4-diol, hex-3-ene-1,6-diol, dec-5-ene-1,10-diol and the like.

Especially suitable for the process of the invention are allyl alcohol, but-3-en-1-ol and 1,4-but-2-enediol.

The term "metathesis catalyst" refers here and below to a compound which has the following structure

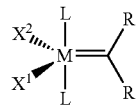

in which M is osmium or ruthenium, R stands for identical or different organic radicals with a great breadth of structural variation, $X^1$ and $X^2$ are anionic ligands, and L represents alike or different, neutral electron donors. The common term "anionic ligands" refers in the literature for such metathesis catalysts in every case to ligands of the kind which, when considered in a state removed from the metal centre, have a negative charge with a closed electron shell.

Such catalysts are known, for example, from WO-A-96/04289 and WO-A-97/06185.

Known from WO-A-00/71554, additionally, is a group of catalysts which are referred to in the art as "Grubbs(II) catalysts":

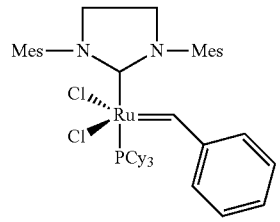

Other metathesis catalysts are described, for example, in WO 99/51344, WO 00/15339, WO 00/71554, WO 02/079126, WO 02/79127, WO 02/083742 and, for example, in Angew. Chem. 1995, 107(18), 2179; J. Am. Chem. Soc. 1995, 117, 5503; J. Am. Chem. Soc. 1996, 118, 100; Chem. Eur. J. 2001, 7, 3236; Organometallics 2000, 19(11), 2055; J. Am. Chem. Soc. 1999, 121, 2674; Organic Letters 1999, 1(6), 953; J. Am. Chem. Soc. 2003, 125, 10103; J. Am. Chem. Soc. 2003, 125, 2546; J. Am. Chem. Soc. 2001, 123, 6543. Further examples of Grubbs(II) catalysts are described, for example, in WO 02/14376, WO 03/011875, WO 03/044060, WO 04/035596, U.S. Pat. No. 6,620,955 and, for example, in J. Am. Chem. Soc. 1999, 121, 791; J. Am. Chem. Soc. 2000, 122, 8168; Tetrahedron Letters 2000, 41, 9973; Tetrahedron 2003, 59, 6545; Synlett 2001, 3, 430; Adv. Synth. Catal. 2003, 345, 572; Synlett 2004, 4, 667; Eur. J. Org. Chem. 2003, 963; Chem. Eur. J. 2004, 10, 2029.

Particularly suitable for processes of the invention are benzylidenebis(tricyclohexylphosphine)dichlororuthenium (1st generation Grubbs catalyst), 1,3-bis(2,4,6-trimethylphenyl)-2-(imidazolidinylidene)(dichlorophenylmethylene)(tricyclohexylphosphine)-ruthenium (2nd generation Grubbs catalyst), (1,3-bis(2,4,6-trimethylphenyl)-2-imidazolidinylidene)dichloro(o-isopropoxyphenylmethylene)ruthenium (2nd generation Hoveyda-Grubbs catalyst) and 1,3-bis(2,4,6-trimethylphenyl)-4,5-dihydroimidazol-2-ylidene[2-(i-propoxy)-5-N,N-dimethylaminosulphonyl)phenyl]methyleneruthenium(II)-dichloride (Zannan catalyst).

Very particular preference is given to complex compounds of the following general formulae:

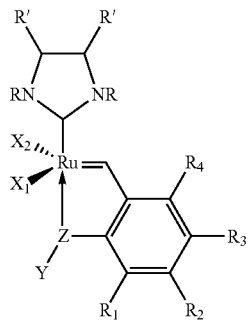 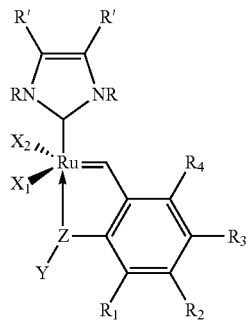

In these formulae

Z is —O—, —S—, —S(O)— and S(O)$_2$—, $X_1$ and $X_2$ adopt the radicals indicated above;

Y, R, R' and $R_1$ to $R_4$ are radicals, selectable independently of one another, from the group of hydrogen, $(C_1$-$C_8)$-alkyl, $(C_1$-$C_8)$-alkoxy, $(C_6$-$C_{18})$-aryloxy, HO—$(C_1$-$C_8)$-alkyl, $(C_2$-$C_8)$-alkoxyalkyl, $(C_6$-$C_{18})$-aryl, $(C_7$-$C_{19})$-aralkyl, $(C_3$-$C_{18})$-heteroaryl, $(C_4$-$C_{19})$-heteroaralkyl, $(C_1$-$C_8)$-alkyl-$(C_6$-$C_{18})$-aryl, $(C_1$-$C_8)$-alkyl-$(C_3$-$C_{18})$-heteroaryl, $(C_3$-$C_8)$-cycloalkyl, $(C_1$-$C_8)$-alkyl-$(C_3$-$C_8)$-cycloalkyl, $(C_3$-$C_8)$-cycloalkyl-$(C_1$-$C_8)$-alkyl. Furthermore, the radicals R' and $R_1$ to $R_4$ may independently of one another have the following definitions: (cyclo)alkylthio, (hetero)arylthio, alkyl/arylsulphonyl, alkyl/arylsulphinyl, in each case optionally substituted by $(C_1$-$C_8)$-alkyl, $(C_1$-$C_8)$-alkoxy, $(C_6$-$C_{18})$-aryloxy, HO—$(C_1$-$C_8)$-alkyl, $(C_2$-$C_8)$-alkoxyalkyl, $(C_6$-$C_{18})$-aryl, perfluoroalkyl, halogen, $(C_1$-$C_8)$-acyloxy, $(C_1$-$C_8)$-acyl $(C_1$-$C_8)$-alkoxycarbonyl, $(C_1$-$C_8)$-alkylsulphonyl or $(C_1$-$C_8)$-alkylsulphinyl, $(C_6$-$C_{18})$-arylsulphonyl or $(C_6$-$C_{18})$-arylsulphinyl.

$R_1$ to $R_4$ may likewise be a nitro group, sulphate, amine, ammonium salt, phosphate and phosphonium salt.

the radicals R' may be linked with one or more of the radicals $R_1$ to $R_4$ in cyclic compounds. The radical $R_1$ may also be linked with the radical Y to form a (hetero) cyclic compound.

Examples of the abovementioned compounds are:

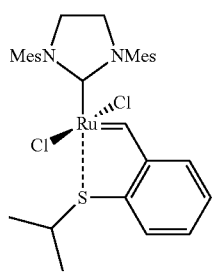 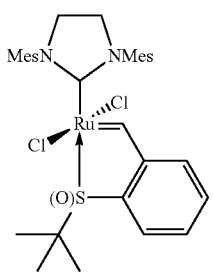

-continued

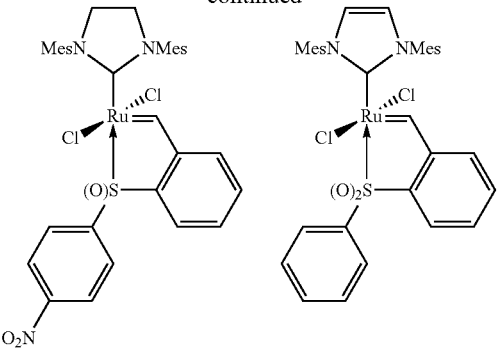

A feature of the process of the invention is that under the reaction conditions of the cross-metathesis there is isomerization of the resultant hydroxyl-functional compound: the metathesis catalyst present in the reaction mixture is converted under the reaction conditions into an isomerization catalyst (a ruthenium hydride species is formed), and so the hydroxyl-functional intermediate compound is isomerized to the corresponding aldehyde-functional compound.

The aldehyde-functional compound resulting in this way is modified in situ, by reaction with a suitable reactant, in such a way that the aldehyde group is 'protected' and therefore effectively prevents further reaction of the resultant aldehyde-functional compound under the reaction conditions of the cross-metathesis and isomerization.

With the process of the invention it is possible to limit the amount of unwanted hydroxyl-functional compound in this way to less than 10% by weight of the products formed.

The process of the invention offers a simple and economically advantageous process for preparing aldehyde-functional fatty acids or fatty acid derivatives in high yield without significant amounts of by-products (i.e. less than 10% by weight, based on the products formed), starting from starting materials based on renewable raw materials.

The particular feature associated with the process of the invention is that no separate isomerization catalyst is needed in order to achieve the object on which the invention is based. Nevertheless, though, it is also possible to add a specific isomerization catalyst to the reaction mixture in addition, in order, for example, to increase the yields still further.

The process of the invention is of particular industrial interest especially in the field of the preparation of starting products for high-performance plastics, such as high-performance polyamides, for example.

As the reactant which acts as a compound forming protective groups with respect to the aldehyde group of the aldehyde-functional compounds, it is possible to select all of the compounds that are known per se to the skilled person and which form a protective group with the aldehyde group of the aldehyde-functional compounds.

Under the term "protective group" there is understood a group which chemically modifies an initially reactive functional group (in this case aldehyde) in such a way that it no longer participates in the reaction events under the prevailing reaction conditions. A further feature of a "protective group" is that it can be removed subsequently under mild conditions (that is, under reaction conditions different from those prevailing when the protective group is formed) and completely, with the original functionality released (i.e. it is a "stable protective group").

Examples of common protective groups and the mechanism for their formation are known from the monograph 'Protecting Groups', Kocienski Philip J., Thieme 2008, and also from 'Protecting Groups in Organic Synthesis', Hanson, James R., Wiley VCH 1999.

The reactant which acts as a compound forming protective groups with respect to the aldehyde group of the aldehyde-functional compounds is more preferably selected from the group consisting of amines and also saturated organic compounds having at least two hydroxyl groups, thiol groups, or one hydroxyl group and one thiol group.

With particular preference the saturated organic compound having at least two hydroxyl groups is ethylene glycol, glycerol, 1,3-propanediol or propylene glycol.

The amine is more preferably an alkylamine, more particularly butylamine.

The formation of the protective group with a saturated organic compound having at least two hydroxyl groups as reactant is illustrated below, taking as an example that of ethylene glycol with n-undecanal as aldehyde-functional compound: under the above-stated reaction conditions, ethylene glycol reacts with n-undecanal to form 2-decyl[1,3]-dioxolane (formation of the corresponding full cyclic acetal).

In the case of amines as a reactant forming protective groups, for example, butylamine reacts as amine with n-undecanal as aldehyde-functional compound to form an n-undecylidenebutan-1-amine (formation of the corresponding imine).

In one particularly preferred embodiment of the present invention the olefinic compound containing at least one hydroxyl group and at least one C—C double bond is present in excess relative to the at least monounsaturated fatty acid or the at least monounsaturated fatty acid derivative.

This embodiment has the advantage that even less self-metathesis takes place.

A further, very particularly preferred embodiment relates to what is called a two-stage process. In this case the cross-metathesis reaction is carried out first at a temperature between 0 and 60° C. The resulting mixture is then brought to a temperature between 80 and 120° C. This two-step process—that is, first the reaction regime at comparatively low temperature and the subsequent heating to a markedly higher temperature—has the advantage that, with a simple change to the reaction regime, the yield is shifted significantly, through isomerization of the hydroxyl-functional compound, in the direction of the aldehyde-functional compound; the fraction of hydroxyl-functional compound is very low and is less than 5%. In the simplest case, neither compounds nor solvents are added to or withdrawn from the reaction mixture; all that is done is that the temperature is increased very rapidly to the aforementioned range.

In a further, preferred embodiment of the present invention the reaction is carried out in the presence of at least solvent.

In principle it is possible to select all of the solvents that are suitable for the metathesis reaction and that do not deactivate the catalyst employed or adversely affect the reaction in any other way whatsoever. Preferred solvents include but are not limited to dichloromethane, benzene, toluene, methyl ethyl ketone, acetone, tetrahydrofuran, tetrahydropyran, dioxane, cyclohexane, methanol, ethanol, propanol, isopropanol, butanol, "all alcohols" and all aliphatic and alicyclic hydrocarbons with different carbon numbers, and also all halogenated hydrocarbons. In certain cases, when the olefinic compound containing at least one hydroxyl group and at least one C—C double bond is able itself to act as solvent, as in the case, for example, of but-3-en-1-ol or but-3-ene-1,4-diol, it is also possible to forego the addition of a further, additional solvent.

Not considered as solvents in the aforementioned sense are amines, hydroxyl thiols, dithiols and saturated organic compounds having at least two hydroxyl groups, such as, for example, ethylene glycol, glycerol, 1,3-propanediol or propylene glycol, since at more than 60° C. unsaturated diols or polyols act not as solvents but as a reactant with protective-group function, and react with the aldehyde-functional compound produced, as disclosed above.

Particular preference is given to selecting a solvent which has a dipole moment of between 0 and 5 debyes. Very particular preference is given to a dipole moment of between 0 and 2.5 debyes.

Examples of such a solvent are dichloromethane (1.60 D), 1,2-dichloroethane (1.48 D), toluene (0.375 D), THF (1.75 D, measured as a 25% strength solution in benzene), 1-butanol (1.66 D), 1,2-diethoxyethane (1.99, measured as a 20% strength solution in benzene), and 1,4-dioxane (0 D).

Especially preferred are tetrahydrofuran, isopropanol and 1-butanol.

In another embodiment of the invention the cross-metathesis reaction is carried out in homogeneous phase. This means that there is no phase separation and that the reactants are not present in a suspension or dispersion.

The homogeneous reaction regime has the advantage that increased cross-metathesis yields are observed.

The amount of the metathesis catalyst, based on the at least monounsaturated fatty acid or at least monounsaturated fatty acid derivative used, is dependent on the nature and also on the catalytic activity of the specific catalyst. The amount of catalyst used is typically 1 to 1000 ppm noble metal, preferably 2 to 500 ppm, more particularly 5 to 250 ppm, based on the fatty acid or fatty acid derivative employed.

The reaction time is dependent on a series of factors, as for example on the type of monounsaturated fatty acid or at least monounsaturated fatty acid derivative used, on the nature of the catalyst, on the catalyst concentration used and on the reaction temperature. Typically the reaction is at an end within three hours under standard conditions. The progress of the metathesis can be monitored by means of standard analysis, such as by GC/MS or HPLC/MS measurements, for example.

In order to improve the isomerization, in other words to shift the product proportions in the direction of aldehyde-functional compound, it is additionally possible to add additives that are known per se to the skilled person, such as hydrides, for example, or bases, to the reaction mixture.

The example which follows serves to illustrate the invention, without confining the invention thereto or restricting the invention in any other way.

1. General Information

Solvents and chemicals. The following commercial solvents and chemicals were used: acetone (99.5% GPR Rectapur from VWR Int., Art. No. 20065.470), benzylidenebis(tricyclohexylphosphine)dichlororuthenium (GI, 1st generation Grubbs catalyst from Aldrich, Art. No. 579726), 1,3-bis(2,4,6-trimethylphenyl)-2-(imidazolidinylidene)(dichlorophenylmethylene)(tricyclohexylphosphine)ruthenium (GII, 2nd generation Grubbs catalyst from Aldrich, Art. No. 569747), (1,3-bis(2,4,6-trimethylphenyl)-2-imidazolidinylidene)dichloro(o-isopropoxyphenylmethylene)-ruthenium (HGII, 2nd generation Hoveyda-Grubbs catalyst from Aldrich, Art. No. 569755), 1,3-bis(2,4,6-trimethylphenyl)-4,5-dihydroimidazol-2-ylidene[2-(i-propoxy)-5-N,N-dimethylaminosulphonyl)phenyl]methyleneruthenium(II) dichloride (ABCR, 96% from ABCR, Art. No. AB173300), 1-butanol (99.9% from Sigma-Aldrich, Art. No. 537993), 2-butene-1,4-diol (≧98.0% from Fluka, Art. No. 03781), 1,2- diethoxyethane (98% from Alfa Aesar, Art. No. L14283), diethyl ether (99% GPR Rectapur from VWR Int., Art. No. 23809.363), 1,2-dimethoxyethane (≧98.0% from Fluka, Art. No. 38570), 2,4-dinitrophenylhydrazine (97% from Aldrich, Art. No. D199303), 1,4-dioxane (anhydrous, 99.8% from Aldrich, Art. No. S39401-018), ethyl vinyl ether (99% from Aldrich, Art. No. 422177), n-hexane (95.0% AnalaR Normapur from VWR Int., Art. No. 24577.367), n-hexane (≧97.0% Chromasolv® for HPLC from Sigma-Aldrich, Art. No. 34859), copper(II) sulphate hydrate (98% from Aldrich, Art. No. 209201), methanol (≧99.9% Chromasolv® for LC-MS from Fluka, Art. No. 34966), sodium hydride (60% dispersion in mineral oil from Aldrich, Art. No. 452912), sodium hydroxide (≧99% from Carl Roth, Art. No. 6771-3), methyl oleate (99% SAFC™ from Sigma-Aldrich, Art. No. S45393-118), 2-propanol (99.9% Chromasolv® plus for HPLC from Sigma-Aldrich, Art. No. 650447), Schiff's reagent (Fluka, Art. No. 84655), sulphuric acid (95-97% from Fluka, Art. No. 84718), tetradecane (olefin-free, ≧99% from Fluka, Art. No. 87140), tetrahydrofuran (Rotisolv® for HPLC from Carl Roth, Art. No. 7344.2), tributylamine (≧98.5% from Aldrich, Art. No. 471313), undecanal (97% from Alfa Aesar, Art. No. A16101), trans-2-undecen-1-ol (96% from ABCR, Art. No. AB125432), potassium sodium tartrate tetrahydrate (99% from Sigma-Aldrich, Art. No. 217255), o-xylene (98.0% from Fluka, Art. No. 95663).

Purification and drying took place—where necessary—in accordance with standard laboratory methods.

Analytical Instruments and Methods

Thin-layer chromatography: The thin-layer chromatographic investigations (TLC) were carried out using silica gel/aluminium foils (layer thickness 0.2 mm from Fluka, Art. No. 60800) The separations took place in a chamber saturated with hexane/diethyl ether (1:1) as eluent over a separation path of 8-10 cm. The substance zones were visualized with permanganate reagent. TLC detection of the aldehydes was carried out with dinitrophenylhydrazine reagent (mixture of 1 g of 2,4-dinitrophenylhydrazine, 25 ml of ethanol, 8 ml of water and 5 ml of concentrated sulphuric acid).

Column chromatography: column chromatographic separations were carried out on silica gel 60, particle size 35-70 µm (Fluka, Art. No. 60738). A chromatographic column with a length of 40 cm and an internal diameter of 2 cm was used. The eluent used was a hexane/diethyl ether (9:1) mixture.

Infrared spectroscopy. IR spectra were recorded using a Bruker EQUINOX 55 FTIR spectrometer with an ATR cell, in the wavenumber range from 4600 to 600 cm$^{-1}$.

NMR spectroscopy: The $^1$H NMR ($^{13}$C NMR) spectra were recorded using a Bruker AVANCE DPX ($^1$H: 300 MHz/$^{13}$C: 75.5 MHz). The standard used for the chemical shift δ was the signal of tetramethylsilane (TMS, δ=0.00 ppm). The coupling constants (J) are reported in hertz (Hz). The coupling patterns were abbreviated as follows: s=singlet; d=doublet; t=triplet; q=quartet; m=multiplet.

Gas chromatography (GC): gas-chromatographic investigations took place using a GC-2010 (Shimadzu) chromatograph equipped with autosampler, flame ionization detector (FID) and GC capillary column Stabilwax® (30 m×0.25 mm×0.25 µm, Restek, Art. No. 10623). Measurements were carried out in split mode (split rate 1:45) with hydrogen as carrier gas (flow rate 1 ml/min, linear carrier gas velocity 31.4 cm/sec). Temperature programme for GC oven: start temperature 95° C., hold for 1 min; heat to 220° C. at 8° C./min, hold for 4 min; heat to 248° C. at 8° C./min, hold for 7 min. Detector and injector temperatures were 250 and 220° C.

GC-MS (EI): GC-MS EI measurements (70 eV) were carried out using a VARIAN 3900 GC with Saturn 2100T Ion trap mass detector and also GC capillary column Factor-Four™ VF-5ms (30 m×0.25 mm×0.25 µm, Varian, Art. No. CP8944). Measurements took place in the mass range from 40 to 650 m/z at a rate of 1.0 scan/s. Measurements were carried out with and without split (split rate 1:50) with helium as carrier gas (flow rate 1 ml/min). Temperature programme for GC oven: start temperature 95° C., hold for 1 min; heat to 220° C. at 15° C./min, hold for 4 min; heat to 300° C. at 15° C./min, hold for 2 min. Injector temperature was 250° C., injection volume 1 µl. The sample solutions were prepared in n-hexane (HPLC purity grade) with a concentration of 1 mg/ml.

Electrospray ionization (ESI-positive) mass spectroscopy: Measurements were carried out using a VARIAN 500-MS ion-trap spectrometer in full scan mode (mass range 40-650 m/z). Analytes were dissolved in methanol for LC-MS (concentration 1 mg/ml) and applied directly using a syringe pump.

Gel permeation chromatography (GPC): The molecular weights were determined using an LC-20AD chromatograph from Shimadzu, equipped with a SIL-20A autosampler, CTO-20A oven, DGU-20A$_3$ degasser and RID-10A refractive index detector. Measurements took place isocratically at 50° C. with a PL gel 5 µm Mixed-D GPC column (300 mm×7.5 mm×5 µm, Polymerlabs, Art. No. PL1110-6504) with THF as eluent (flow rate 1.0 ml/min). The column was calibrated using linear poly(methyl methacrylate) standards (Polymer Kit from Polymer Standards Service PPS, Germany, $M_p$ 102-981.000 Da, Art. No. PSS-mmkith).

Detection of aldehydes with staining reagents: for the qualitative detection of aldehydes in the reaction mixtures, Fehling's solution (prepared freshly according to standard laboratory methods) and Schiff's reagent (Fluka) were used.

Yields: reported yields—unless otherwise indicated—relate to the products calculated by means of GC-chromatographic data.

Glassware and apparatus: For carrying out the reactions on the 1 ml scale, test tubes were used with standard NS14/23 ground joints and PE stoppers (total volume 10 ml, from VWR, Art. No. 212-1622). Reactions were carried out in a silicone oil bath on a hot plate with an integrated IKA® RET Basic magnetic stirrer and IKA® ETS-D5 electronic contact thermometer.

The reactions on the 2 ml scale were carried out in a Carousel Reaction Station™ RR98072 from Radleys Discovery Technologies.

The isomerization experiments under an inert atmosphere were carried out in 3 ml test tubes with a screw-top closure and septum (Supelco from Aldrich, Art. No. 33297). The reaction mixture was flushed with the inert gas (PR Nitrogen BIP-X10S from Air Products) through the septum by means of cannulas. The reaction mixtures were thermally conditioned in a heating block (Sigma-Aldrich, Art. No. Z210188-1EA) with the aid of a hot plate with an IKA® RET Basic integrated magnetic stirrer and IKA® ETS-D5 electronic contact thermometer. For all other isomerizations, the glassware and apparatus used were the same as for the reactions on the 1 ml scale (see description above).

2. Synthesis Directions

General Directions

Reactions on the 2 ml scale: Syntheses took place with 2 ml of methyl oleate under the following reaction conditions: the reactions were carried out in different solvents (acetone, 1-butanol, 1,4-dioxane, 2-propanol, THF). All of the reactions were carried out with two different ratios of butenediol (3 and 5 equivalents, based on methyl oleate) and at two different temperatures (40 and 60° C.). Ruthenium-based metathesis catalysts (available commercially from Aldrich or ABCR, and test specimens from Evonik Degussa GmbH) were tested for all ratios and temperatures. No additives were used.

General method: In a reaction vessel the mixture of 2 ml (5.9 mmol) of methyl oleate, the corresponding amount of 2-butene-1,4-diol (1.46 ml or 2.43 ml), 0.2 ml of tetradecane (internal standard) and 2 ml of the corresponding solvent is prepared and shaken. Thereafter a blank sample is taken for GC measurement. After sampling has taken place, the corresponding catalyst (2 mol %) is added and the reaction vessel is placed in the temperature-conditioned carousel reactor. The mixture is heated for 4 hours and stirring is continued, and after that the final GC sample is taken for kinetic determinations. After 4 hours the reaction is halted by addition of 2 ml of ethyl vinyl ether.

Isomerization of trans-2-undecen-1-ol. Syntheses took place with 0.1 ml of trans-2-undecen-1-ol under nitrogen atmosphere and without inert gas atmosphere. The reactions were carried out in different solvents (1-butanol, 1,4-dioxane, 1,2-dimethoxyethane, 1,2-diethoxyethane, ethylene glycol) and also without solvent. The different concentrations of 2-undecen-1-ol (dilution 1:3, 1:10, 1:20, 1:30, 1:50) and different temperatures (40, 60, 80, 100 and 120° C.) were investigated. Ruthenium-based metathesis catalysts (available commercially from Aldrich and ABCR) were tested for all ratios and temperatures.

General method: A) Isomerization under an inert atmosphere: In a test tube the mixture of 0.1 ml (0.49 mmol) of trans-2-undecen-1-ol and 0.02 ml of tetradecane (internal standard) is prepared and mixed. If the reaction is being carried out without solvent, a blank sample is taken for GC measurement. In the case of the procedure with solvent, a blank sample for GC measurement is taken only after the addition of the corresponding solvent. After sampling has taken place, the reaction mixture is flushed with nitrogen for about 5 minutes by means of cannulas (room temperature), after which the catalyst (0.5 mol %) is added and the reaction vessel is placed in a thermally conditioned oil bath and stirred by means of a magnetic stirrer. The reaction is carried out with continuous flushing with nitrogen. The samples for GC, GC-MS and GPC measurements are taken through the septum using a microliter syringe (10 µl, Hamilton via Sigma-Aldrich, Art. No. 21316) after 5, 20, 30, 60 and 180 minutes of reaction.

B) Isomerization without an inert atmosphere: In a test tube the mixture of 0.1 ml (0.49 mmol) of trans-2-undecen-1-ol and 0.02 ml of tetradecane (internal standard) is prepared and mixed. If the reaction is being carried out without solvent, a blank sample is taken for GC measurement. In the case of the procedure with solvent, a blank sample for GC measurement is taken only after the addition of the corresponding solvent. After sampling has taken place, the catalyst (0.5 mol %) is added and the reaction vessel is placed in a thermally conditioned oil bath and stirred by means of a magnetic stirrer. The samples for GC, GC-MS and GPC measurements are taken after 5, 20, 30, 60 and 180 minutes of reaction.

Isomerization of a mixture of 2-undecen-1-ol and methyl 11-hydroxy-9-undecenoate: The mixture was obtained by means of cross-metathesis of methyl oleate and butenediol. After removal of the solvent on a rotary evaporator, where necessary, a reagent forming protective groups was added, without further working-up steps and without addition or removal of components, and the reaction was carried out further as described under "Isomerization of trans-2-undecen-1-ol".

Sample preparation for GC measurements: The 2 ml sample vial for the GC measurements was filled with 10-30 µl of reaction mixture and 100 µl of ethyl vinyl ether and diluted with 0.89-1.37 ml of THF (HPLC purity grade).

WORKING EXAMPLE

A mixture of 2-undecen-1-ol and methyl 11-hydroxy-9-undecenoate (0.5 ml, obtained from the cross-metathesis of methyl oleate with butenediol; composition: 8.7% methyl oleate, 13.2% 9-octadecene and 1,18-dimethyl-9-octadecenedicarboxylic acid, 61.2% alcohol cross-metathesis products, 16.9% aldehyde cross-metathesis products) and 4.5 ml of ethylene glycol are combined. Further samples are taken for GC, GC-MS and GPC. By means of a magnetic stirrer, the reaction mixture is stirred at 120° C. for 60 minutes. After 5, 30 and 60 minutes the samples for GC, GC-MS and GPC measurements are taken and the reaction is stopped. Conversion of both alcohol cross-metathesis products after 60 minutes: 90%. Total yield (over two steps) of the 2-decyl-[1,3]dioxolane (protected undecanal): 67%; total yield (over two steps) of the methyl undecanoate-11-[1,3]dioxolane (protected methyl 11-oxoundecanoate): 69%; by-products (oligomers): 5%.

3. Analytical Data

GC measurements. The components of the reaction mixture were recorded with the following retention times: undecanal ($t_R$=7.34 min), 2-undecen-1-ol ($t_R$=11.54 min), methyl 11-hydroxy-9-undecenoate ($t_R$=19.88 min), methyl 11-oxoundecanoate ($t_R$=15.90 min), 9-octadecene ($t_R$=10.29 min), 1,18-dimethyl-9-octadecenedicarboxylic acid ($t_R$=29.27 min), tetradecane ($t_R$=4.76 min), 2-butene-1,4-diol ($t_R$=13.16 min), methyl oleate ($t_R$=18.09 min).

GC-MS (EI) measurements. The components of the reaction mixture were recorded with the following retention times: undecanal ($t_R$=5.65 min), 2-decyl-[1,3]-dioxolane ($t_R$=7.87 min), 2-undecen-1-ol ($t_R$=6.19 min), methyl 11-hydroxy-9-undecenoate ($t_R$=8.88 min), methyl 11-oxoundecanoate ($t_R$=8.42 min), 9-octadecene ($t_R$=9.50 min), 1,18-dimethyl-9-octadecenedicarboxylic acid ($t_R$=16.78 min), tetradecane ($t_R$=6.44 min), 2-butene-1,4-diol ($t_R$=2.68 min), methyl oleate ($t_R$=12.99 min).

Undecanal. GC-MS (EI, m/z, %): 170.9 ($M^{+\cdot}$, 3), 123.0 (6), 108.9 (13), 94.9 (45), 81.8 (60), 67.0 (98), 55.0 (65), 41.0 (100). MS (ESI-positive, $CH_3OH$, m/z): 193.7 ($MNa^+$, calc. 193.3).

2-Undecen-1-ol. GC-MS (EI, m/z, %): 151.9 ($M^{+\cdot}$-$H_2O$, 5), 137.9 (2), 123.0 (10), 109.0 (23), 95.2 (100), 83.0 (75), 67.2 (28), 57.1 (22). MS (ESI-positive, $CH_3OH$, m/z): 193.7 ($MNa^+$, calc. 193.3).

Methyl 11-hydroxy-9-undecenoate. GC-MS (EI, m/z, %): 196.8 ($M^{+\cdot}$-$H_2O$, 20), 164.0 (22), 147.0 (28), 136.0 (25), 120.9 (25), 110.8 (30), 98.0 (70), 79.0 (45), 66.9 (67), 55.0 (100), 41.0 (70). MS (ESI-positive, $CH_3OH$, m/z): 237.1 ($MNa^+$, calc. 237.3).

Methyl 11-oxoundecanoate. GC-MS (EI, m/z, %): 214.8 ($M^{+\cdot}$, 65), 183.0 (30), 171.0 (45), 164.9 (17), 139.0 (90), 121.0 (42), 111.0 (20), 97.0 (30), 80.9 (58), 73.9 (70), 66.9 (35), 55.0 (90), 43.0 (100). MS (ESI-positive, $CH_3OH$, m/z): 237.1 ($MNa^+$, calc. 237.3).

9-Octadecene. GC-MS (EI, m/z, %): 252.0 ($M^{+\cdot}$, 3), 208.0 (2), 193.9 (2), 180.0 (3), 166.0 (4), 152.0 (3), 138.0 (5), 124.9 (20), 110.9 (40), 97.0 (100), 82.8 (87), 57.0 (56), 55.1 (90).

1,18-Dimethyl-9-octadecenedicarboxylic acid. GC-MS (EI, m/z, %): 341.0 ($M^{+\cdot}$, 6), 308.2 (52), 290.2 (16), 276.2 (100), 248.3 (26), 189.2 (7), 175.2 (9), 161.2 (14), 147.2 (38), 134.1 (36), 119.2 (20), 109.2 (25), 98.1 (48), 83.0 (73), 67.2 (77), 55.0 (98). MS (ESI-positive, CH$_3$OH, m/z): 363.3 (MNa$^+$, calc. 363.5).

2-Decyl-[1,3]dioxolane (the cyclic acetal of the undecanal): GC-MS (EI, mz, %): 213.1 (M$^{+\cdot}$, 5), 150.9 (1), 122.9 (1), 109.0 (1), 97.0 (2), 80.9 (1), 73.0 (100), 55.0 (5), 45.0 (13).

Methyl 11-undecanoate-[1,3]dioxolane (the cyclic acetal of methyl 11-oxoundecanoate): MS (ESI-positive, CH$_3$OH, m/z): 281.2 (MNa$^+$, calc. 281.4).

The invention claimed is:

1. A process for preparing an aldehyde-functional compound, comprising:
   cross-metathesis reacting and isomerizing an olefinic compound comprising at least one hydroxyl group and at least one C—C double bond
   with at least one at least monounsaturated fatty acid or with one at least monounsaturated fatty acid derivative
   in the presence of a metathesis catalyst
   at a temperature of not more than 180° C.
   and also in the presence of at least one reactant acting as a compound forming at least one protective group with respect to the aldehyde group of the aldehyde-functional compound.

2. The process of claim 1, wherein the reactant is at least one selected from the group consisting of an amine and a saturated organic compound having at least two hydroxyl groups.

3. The process of claim 2, wherein the saturated organic compound having at least two hydroxyl groups is present and is ethylene glycol, glycerol, 1,3-propanediol, or propylene glycol.

4. The process of claim 2, wherein the amine is present and is a primary alkylamine.

5. The process of claim 1, wherein the olefinic compound is present in excess relative to the at least monounsaturated fatty acid or the at least monounsaturated fatty acid derivative.

6. The process of claim 1, wherein the cross-metathesis reacting is carried out first at a temperature between 0 and 60° C. to obtain a resulting mixture, and then the resulting mixture is brought to a temperature between 80 and 120° C.

7. The process of claim 1, wherein the olefinic compound is present in a ratio of 1 to 10 equivalents, based on the at least monounsaturated fatty acid derivative.

8. The process of claim 1, wherein the cross-metathesis reacting is carried out in the presence of at least one solvent.

9. The process of claim 8, wherein the solvent has a dipole moment of between 0 and 5 debyes.

10. The process of claim 1, wherein the cross-metathesis reacting is carried out in homogeneous phase.

11. The process of claim 1, wherein the at least monounsaturated fatty acid is present and is selected from the group consisting of oleic acid, undecylenic acid, palmitoleic acid, petroselinic acid, erucic acid, icosenoic acid, vernolic acid, ricinoleic acid, linoleic acid, and linolenic acid.

12. The process of claim 1, wherein the at least monounsaturated fatty acid derivative is present and is at least one ester formed, by esterifying
   at least one acid selected from the group consisting of oleic acid, undecylenic acid, palmitoleic acid, petroselinic acid, erucic acid, icosenoic acid, vernolic acid, ricinoleic acid, linoleic acid, and linolenic acid,
   with at least one alcohol selected from the group consisting of methanol, ethanol, propanol, glycerol, and glycol.

13. The process of claim 1, wherein the olefinic compound is selected from the group consisting of allyl alcohol, but-3-en-1-ol, and 1,4-but-2-enediol.

14. The process of claim 2, wherein the amine is present and is a primary aliphatic alkylamine having 2-10 carbon atoms.

15. The process of claim 2, wherein the amine is present and comprises butylamine.

16. The process of claim 1, wherein the olefinic compound is present in a ratio of 2 to 4 equivalents, based on the at least monounsaturated fatty acid derivative.

17. The process of claim 2, wherein the cross-metathesis reacting is carried out first at a temperature between 0 and 60° C. to obtain a resulting mixture, and then the resulting mixture is brought to a temperature between 80 and 120° C.

18. The process of claim 3, wherein the cross-metathesis reacting is carried out first at a temperature between 0 and 60° C. to obtain a resulting mixture, and then the resulting mixture is brought to a temperature between 80 and 120° C.

19. The process of claim 4, wherein the cross-metathesis reacting is carried out first at a temperature between 0 and 60° C. to obtain a resulting mixture, and then the resulting mixture is brought to a temperature between 80 and 120° C.

20. The process of claim 5, wherein the cross-metathesis reacting is carried out first at a temperature between 0 and 60° C. to obtain a resulting mixture, and then the resulting mixture is brought to a temperature between 80 and 120° C.

* * * * *